United States Patent
Khanmamedova et al.

(10) Patent No.: US 10,583,422 B2
(45) Date of Patent: *Mar. 10, 2020

(54) CATALYST WITH IMPROVED ACTIVITY/SELECTIVITY FOR LIGHT NAPHTHA AROMATIZATION

(71) Applicant: SAUDI BASIC INDUSTRIES CORPORATION, Riyadh (SA)

(72) Inventors: Alla Khanmamedova, Sugar Land, TX (US); Scott Stevenson, Houston, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,910

(22) Filed: Jul. 31, 2019

(65) Prior Publication Data

US 2019/0351395 A1    Nov. 21, 2019

Related U.S. Application Data

(62) Division of application No. 15/035,505, filed as application No. PCT/US2014/064250 on Nov. 6, 2014, now Pat. No. 10,207,255.

(60) Provisional application No. 61/907,466, filed on Nov. 22, 2013.

(51) Int. Cl.

| | |
|---|---|
| C07C 15/02 | (2006.01) |
| B01J 29/04 | (2006.01) |
| B01J 37/18 | (2006.01) |
| C10G 45/10 | (2006.01) |
| B01J 29/44 | (2006.01) |
| B01J 37/00 | (2006.01) |
| C10G 35/095 | (2006.01) |
| C10G 45/70 | (2006.01) |
| C07C 5/32 | (2006.01) |
| B01J 37/08 | (2006.01) |
| B01J 37/04 | (2006.01) |
| C07C 2/76 | (2006.01) |
| C07C 5/367 | (2006.01) |
| B01J 29/06 | (2006.01) |
| B01J 37/03 | (2006.01) |
| B01J 23/42 | (2006.01) |
| B01J 35/00 | (2006.01) |
| B01J 37/02 | (2006.01) |
| C10G 45/12 | (2006.01) |

(52) U.S. Cl.
CPC ............. B01J 29/047 (2013.01); B01J 23/42 (2013.01); B01J 29/061 (2013.01); B01J 29/44 (2013.01); B01J 35/0006 (2013.01); B01J 37/0009 (2013.01); B01J 37/0215 (2013.01); B01J 37/031 (2013.01); B01J 37/036 (2013.01); B01J 37/04 (2013.01); B01J 37/08 (2013.01); B01J 37/18 (2013.01); C07C 2/76 (2013.01); C07C 5/322 (2013.01); C07C 5/325 (2013.01); C07C 5/367 (2013.01); C07C 15/02 (2013.01); C10G 35/095 (2013.01); C10G 45/10 (2013.01); C10G 45/12 (2013.01); C10G 45/70 (2013.01); B01J 2229/186 (2013.01); C07C 2529/03 (2013.01); C07C 2529/068 (2013.01); C07C 2529/40 (2013.01); C07C 2529/42 (2013.01); C07C 2529/44 (2013.01); C07C 2529/54 (2013.01); C07C 2529/62 (2013.01)

(58) Field of Classification Search
CPC ........ C10G 45/10; C10G 45/12; C10G 45/70; C10G 35/095; C07C 5/325; C07C 5/367; C07C 5/322; C07C 15/02; C07C 2/76; C07C 2529/40; C07C 2529/42; C07C 2529/068; C07C 2529/44; C07C 2529/54; C07C 2529/03; C07C 2529/62
USPC ....... 585/407, 410, 411, 418, 419, 421, 440, 585/444, 654, 660; 208/133, 134, 135, 208/137, 138, 141
See application file for complete search history.

(56) References Cited

U.S. PATENT DOCUMENTS

| | | |
|---|---|---|
| 3,216,789 A | 11/1965 | Breck et al. |
| 3,702,886 A | 11/1972 | Argauer et al. |
| 3,926,782 A | 12/1975 | Plank et al. |
| 4,104,320 A | 8/1978 | Bernard et al. |

(Continued)

FOREIGN PATENT DOCUMENTS

| | | |
|---|---|---|
| EP | 0205300 B1 | 7/1991 |
| WO | 2005003031 A1 | 1/2005 |

(Continued)

OTHER PUBLICATIONS

Aboul-Gheit et al.; "Catalytic para-xylene maximization: III. Hydroisomerization of meta-xylene on H-ZSM-5 catalysts containing differenct platinum contents"; J. Chem. Technol Biotechnol; 1999; 74; pp. 771-777.

(Continued)

*Primary Examiner* — Elizabeth D Wood
(74) *Attorney, Agent, or Firm* — Cantor Colburn LLP

(57) ABSTRACT

In an aspect, a method for the aromatization of hydrocarbons comprises contacting a hydrocarbon feedstream with a catalyst; wherein the catalyst comprises a zeolite comprising Si, Al, and Ge in the framework with Pt deposited thereon; wherein the zeolite further comprises Na; and wherein the catalyst has an Si:Al$_2$ mole ratio of greater than or equal to 125, an Si:Ge mole ratio of 40 to 400, and an Na:Al mole ratio of 0.9 to 2.5, wherein the catalyst has an aluminum content of less than or equal to 0.75 wt % excluding any binder and extrusion aide.

18 Claims, No Drawings

(56) References Cited

U.S. PATENT DOCUMENTS

| | | | |
|---|---|---|---|
| 4,310,440 A | 1/1982 | Wilson et al. | |
| 4,374,296 A | 2/1983 | Haag et al. | |
| 4,417,083 A | 11/1983 | Bernard et al. | |
| 4,435,283 A | 3/1984 | Buss et al. | |
| 4,440,871 A | 4/1984 | Lok et al. | |
| 4,517,306 A | 5/1985 | Buss | |
| 4,560,820 A | 12/1985 | Field | |
| 4,645,586 A | 2/1987 | Buss | |
| 4,652,360 A | 3/1987 | Dessau | |
| 4,652,689 A | 3/1987 | Lambert et al. | |
| 4,830,732 A | 5/1989 | Mohr et al. | |
| 4,837,397 A | 6/1989 | Absil et al. | |
| 4,867,864 A | 9/1989 | Dessau | |
| 4,892,646 A | 1/1990 | Venkat et al. | |
| 4,900,529 A | 2/1990 | Sanchez et al. | |
| 4,908,341 A | 3/1990 | Pruden et al. | |
| 4,954,245 A | 9/1990 | Miller et al. | |
| 4,962,250 A | 10/1990 | Dessau et al. | |
| 5,028,312 A | 7/1991 | Miller et al. | |
| 5,185,484 A | 2/1993 | Del Rossi et al. | |
| 5,209,918 A | 5/1993 | Hellring et al. | |
| 5,210,364 A | 5/1993 | Barri et al. | |
| 5,215,950 A | 6/1993 | Bournonville et al. | |
| 5,227,557 A | 7/1993 | Bournonville et al. | |
| 5,246,688 A | 9/1993 | Faust et al. | |
| 5,268,161 A | 12/1993 | Nakagawa | |
| 5,358,631 A | 10/1994 | Miller et al. | |
| 5,449,450 A | 9/1995 | Bedard | |
| 5,456,822 A | 10/1995 | Marcilly et al. | |
| 5,510,016 A | 4/1996 | Hilbert et al. | |
| 5,518,707 A | 5/1996 | Bedard et al. | |
| 5,633,422 A | 2/1997 | Murray | |
| 5,667,695 A | 9/1997 | Bedard et al. | |
| 5,773,381 A | 6/1998 | Verduijn et al. | |
| 5,885,443 A | 3/1999 | Bogdan et al. | |
| 5,935,415 A | 8/1999 | Haizmann et al. | |
| 5,977,009 A | 11/1999 | Faraj | |
| 5,993,642 A | 11/1999 | Mohr et al. | |
| 6,046,373 A | 4/2000 | Sun | |
| 6,048,449 A | 4/2000 | Bogdan et al. | |
| 6,063,724 A | 5/2000 | Resasco et al. | |
| 6,083,379 A | 6/2000 | Drake et al. | |
| 6,160,191 A | 12/2000 | Smith et al. | |
| 6,177,374 B1 | 1/2001 | Pradhan et al. | |
| 6,245,219 B1 | 6/2001 | Kao | |
| 6,358,400 B1 | 3/2002 | Bogdan et al. | |
| 6,410,473 B1 | 6/2002 | Pinnavaia et al. | |
| 6,486,373 B1 | 11/2002 | Abichandani et al. | |
| 6,740,228 B1 | 5/2004 | Verduijn et al. | |
| 6,784,333 B2 | 8/2004 | Juttu et al. | |
| 6,884,531 B2 | 4/2005 | Dabbousi et al. | |
| 6,914,165 B2 | 7/2005 | Flego et al. | |
| 7,029,572 B2 | 4/2006 | Maesen et al. | |
| 7,029,650 B1 | 4/2006 | Juttu et al. | |
| 7,037,422 B2 | 5/2006 | Maesen et al. | |
| 7,037,871 B1 | 5/2006 | Galperin et al. | |
| 7,153,801 B2 | 12/2006 | Wu | |
| 7,186,871 B2 | 3/2007 | Mitchell et al. | |
| 7,247,593 B2 | 7/2007 | Juttu et al. | |
| 7,307,422 B2 | 12/2007 | Van Helvoort et al. | |
| 7,414,007 B2 | 8/2008 | Gillespie et al. | |
| 7,449,168 B2 | 11/2008 | Juttu et al. | |
| 7,745,675 B2 | 6/2010 | Ellis et al. | |
| 7,902,413 B2 | 3/2011 | Stevenson et al. | |
| 8,153,852 B2 | 4/2012 | Ellis et al. | |
| 8,722,950 B2 | 5/2014 | Van Hal et al. | |
| 8,969,232 B2 | 3/2015 | Mitchell et al. | |
| 8,993,468 B2 | 3/2015 | Stevenson et al. | |
| 9,192,925 B2 | 11/2015 | Mitchell et al. | |
| 9,221,723 B2 | 12/2015 | Khanmamedova et al. | |
| 9,233,884 B2 | 1/2016 | Khanmamedova et al. | |
| 9,782,758 B2 * | 10/2017 | Ghosh | B01J 29/40 |
| 2001/0024635 A1 | 9/2001 | Beck et al. | |
| 2003/0073856 A1 | 4/2003 | Hancu et al. | |
| 2003/0121827 A1 | 7/2003 | Van Den Berge et al. | |
| 2004/0121902 A1 | 6/2004 | Chang et al. | |
| 2004/0200757 A9 | 10/2004 | Takewaki et al. | |
| 2005/0158238 A1 | 7/2005 | Tatsumi et al. | |
| 2005/0197515 A1 | 9/2005 | Juttu et al. | |
| 2005/0209093 A1 | 9/2005 | Chester et al. | |
| 2005/0271582 A1 | 12/2005 | Barea et al. | |
| 2005/0274647 A1 | 12/2005 | Boehmer et al. | |
| 2006/0115415 A1 | 6/2006 | Yuen | |
| 2006/0205990 A1 | 9/2006 | Rice | |
| 2008/0255398 A1 | 10/2008 | Stevenson et al. | |
| 2008/0293988 A1 * | 11/2008 | Mitchell | B01J 29/405 585/500 |
| 2012/0122662 A1 | 5/2012 | Khanmamedova et al. | |
| 2015/0018590 A1 | 1/2015 | Stevenson et al. | |

FOREIGN PATENT DOCUMENTS

| | | |
|---|---|---|
| WO | 2006071873 A1 | 7/2006 |
| WO | 2012075400 A1 | 6/2012 |

OTHER PUBLICATIONS

Bebon et al., "Synthesis of zeolites: study and application of a new process of homogeneous shaking out of the medium to minimize the shear rate during the crystallization", Microporous and Mesoporous Materials, 53 (2002), pp. 13-20.

Gao et al.; "Mechanistic study of organic template removal from ZSM-5 precursors"; Microporous and Mesoporous Materials, 70; (2004); pp. 27-35.

Halgeri; "Disproportionation of Toluene Over a Metal-supported Type L-Zeolite Catalyst"; J. Chem. Tech. Biotechnol.; 1981;31; pp. 541-545.

Hughes et al.; Aromatization of Hydrocarbons over Platinum Alkaline Earth Zeolites; Proceedings of 7th International Zeolite Conference; Tokyo; pp. 725-732; 1986.

Kosslick et al.; "Synthesis and Characterization of Ge-ZSM-5 Zeolites"; J. Phys. Chem.; vol. 97; 1993; pp. 5678-5684.

McVicker et al.; "Effect of Sulfur on the Performance and on the Particle Size and Location of Platinum in Pt/K Hexane Aromatization Catalysts"; Journal of Catalysis; vol. 139; pp. 46-61; 1993.

Napta; Safety Data Sheet; Tesoro; 12 Pages.

Olson et al.; "Chemical and Physical Properties of the ZSM-5 Substitutional Series"; Journal of Catalysis 61; pp. 390-396; 1980.

Pellet; "Hydrogen Transfer Catalysis by Platinum on Zeolites"; J. of Catalysis 177; pp. 40-52; 1998.

Tamm et al.; "Octane Enhancement by Selective Reforming of Light Paraffins"; Catalysis 1987; J.W. Ward (Editor); p. 335-353; 1988.

Tamm et al.; "Selective Catalytic Process for Conversion of Light Naphtha to Aromatics"; Energy Progress; vol. 7, No. 4; pp. 215-222; Dec. 1987.

Van De Water et al.; "Improved Catalytic Activity Upon Ge Incorporation into ZSM-5 Zeilites"; Journal of Catalysis; vol. 223; 2004; pp. 170-178.

International Search Report for International Application No. PCT/US2014/064250; International Filing Date Nov. 6, 2014; dated Feb. 23, 2015; 4 pages.

Komatsu et al.; "Aromatization of butane on Pt—Ge intermetallic compounds supported on JZSM-5"; Applied Catalysis A: General 194-195 (2000); pp. 333-339.

Salguero et al.; Propane transformation over H-ZSM5 zeolite modified with germanium; Catalysis Letter 47; 1997; pp. 143-154.

Written Opinion of the International Search Report for International Application No. PCT/US2014/064250; International Filing Date Nov. 6, 2014; dated Feb. 23, 2015; 8 pages.

* cited by examiner

CATALYST WITH IMPROVED ACTIVITY/SELECTIVITY FOR LIGHT NAPHTHA AROMATIZATION

CROSS REFERENCE TO RELATED APPLICATIONS

This application is a divisional of U.S. patent application Ser. No. 15/035,505, filed May 10, 2016, now U.S. Pat. No. 10,207,255, which is a national stage application of International Application No. PCT/US2014/064250 filed on Nov. 6, 2014, which claims the benefit of U.S. Provisional Application Ser. No. 61/907,466 filed on Nov. 22, 2013, all of which are incorporated herein by reference in their entirety.

BACKGROUND

A zeolite is a crystalline hydrated aluminosilicate that can contain other metals in the framework of the zeolite crystal or that can be deposited, exchanged, or impregnated on the zeolite (i.e. on the surface or in the pores). A method for preparing a zeolite comprises: preparing an aqueous mixture of silicon oxide and sources of oxides of aluminum; and maintaining said aqueous mixture under crystallization conditions until crystals of zeolite form. In the crystalline structure, there are pores and channels that can be interconnected. The dimensions and configuration of these pores and channels allow access by molecules of certain sizes. Zeolites are used as catalysts for, among other things, isomerization, toluene disproportionation, transalkylation, hydrogenation, alkane oligomerization, and aromatization. Aromatization is a multi-step process that can comprise the steps of dehydrogenation of the hydrocarbon, cyclization of the dehydrogenated hydrocarbon, and aromatization of the cyclized hydrocarbon.

One such example of hydrocarbon aromatization is aromatization of naphtha. Naphtha is a mixture mainly of straight-chained, branched, and cyclic aliphatic hydrocarbons, light naphtha having from five to nine carbon atoms per molecule, and heavy naphtha having from seven to twelve carbon atoms per molecule. Typically, light naphtha contains naphthenes, such as cyclohexane and methylcyclopentane, and linear and branched paraffins, such as hexane and pentane. Light naphtha typically contains 60 to 99 weight percent (wt %) of paraffins and cycloparaffins. Light naphtha can be characterized as a petroleum distillate having a molecular weight range of 70 to 150 gram per mole (g/mol), a specific gravity range of 0.6 to 0.9 grams per cubic centimeter (g/cm$^3$), a boiling point range of 50 to 320 degree Fahrenheit (° F.) (10 to 160 degree Celsius (° C.)), and a vapor pressure of 5 to 500 millimeter of mercury (mmHg) at room temperature. Light naphtha can be obtained from crude oil, natural gas condensate, or other hydrocarbons streams by a variety of processes, e.g., distillation.

A zeolite with one or both of improved selectivity and conversion for naphtha aromatization is desirable.

BRIEF SUMMARY

Disclosed herein is a catalyst, methods for making and using the same.

In an embodiment, a catalyst comprises a zeolite comprising Si, Al, and Ge in the framework with Pt deposited thereon; wherein the catalyst has an Si:Al$_2$ mole ratio of greater than or equal to 125, an Si:Ge mole ratio of 40 to 400, and an Na:Al mole ratio of 0.9 to 2.5; wherein the catalyst has an aluminum content of less than or equal to 0.75 wt %; wherein the catalyst is non-acidic.

In another embodiment, a catalyst comprises a zeolite comprising Si, Al, and Ge in the framework with Pt deposited thereon; wherein the zeolite is a medium pore zeolite having an average pore size of 5 to 8 Å; wherein the catalyst has an Si:Al$_2$ mole ratio of 125 to 211, an Si:Ge mole ratio of 40 to 400, and an Na:Al mole ratio of 0.9 to 2.5; wherein the catalyst has an aluminum content of less than or equal to 0.75 wt %; and a Ge content of 0.1 to 3 wt %, based on the total weight of the catalyst excluding any binder and extrusion aide; wherein the catalyst is non-acidic.

In yet another embodiment, a method for the aromatization of hydrocarbons comprises contacting an alkane containing 6 to 12 carbon atoms per molecule with the catalyst.

The above described and other features are exemplified by the following detailed description.

DETAILED DESCRIPTION

In previous methods of preparing a non-acidic catalyst for light naphtha aromatization, a mixture comprising an aluminum source, a silica source, a tetravalent metal, a trivalent metal, or a combination comprising one or more of the foregoing was formed and the pH of the mixture was then adjusted to a low pH of less than or equal to 9 (e.g., in order to obtain the desired amount of tetravalent metal on the catalyst). Materials prepared in this manner are generally acidic. An acidic zeolite catalyst has a number of sites with significant Brønsted or Lewis acidity, and these sites promote cracking of feed components, an undesirable reaction in light naphtha aromatization. Hence, the catalyst is generally subjected to a post-synthesis ion-exchange step where an alkali metal or other basic component is used to neutralize the acid sites by bringing the alkali metal in close proximity to the aluminum. When alkali metals, which have a charge of +1, are used, the molar ratio of alkali metal to aluminum in the resulting non-acidic catalyst will be greater than 0.90, e.g., greater than or equal to 0.95. It was surprisingly discovered that a non-acidic catalyst could be formed from a mixture having a pH value of greater than or equal to 9.5. Not to be bound by theory, it is believed that under such conditions, an increased amount of sodium is present to neutralize the aluminum. It was further surprisingly discovered that although preparing the catalyst at this increased pH can limit the amount of germanium that can be incorporated into the final catalyst, for example, to less than 3 wt % based on the final weight of the catalyst (excluding any binder and extrusion aide), good activity and good selectivity can still be achieved. Good activity is a conversion of greater than or equal to 20% at a temperature of 515° C. and a liquid hourly space velocity of 8.6 reciprocal hours (hr$^{-1}$), preferably, greater than or equal to 30% and good selectivity is a selectivity of greater than or equal to 85%, preferably, greater than or equal to 90%.

The catalyst can be a germanium (Ge) substituted medium pore zeolite, onto which a noble metal (such as platinum) has been deposited. Preferably, the catalyst can be a non-acidic, low aluminum Pt/Ge-ZSM-5 catalyst, e.g., having an amount of aluminum (Al) of less than or equal to 0.75 wt %, for example, 0.45 to 0.7 wt %, based upon a total weight of the final catalyst. As used herein, a non-acidic zeolite refers to a non-acidic zeolite that has substantially all of its cationic sites of exchange, e.g., those typically associated with aluminum, occupied by non-hydrogen cationic species, e.g., alkali or alkaline earth metals such as sodium, potassium, rubidium, cesium, lithium, magnesium, calcium, barium, or a combination comprising one or more of the foregoing; preferably, the alkali metal can comprise sodium. The cationic sites are often responsible for cracking of hydrocarbons into undesired products.

The zeolite can be any of a number of zeolites, where zeolites are crystalline aluminosilicates with a three-dimensional framework containing silica ($SiO_4$) and alumina ($AlO_4$) tetrahedra and can be naturally occurring or synthesized. The zeolite can contain elements other than aluminum and silicon in the crystalline framework. The term "zeolite" includes not only aluminosilicates, but substances in which the aluminum is replaced by other trivalent elements and substances in which silicon is replaced by other tetravalent elements. Zeolites are known catalysts for isomerization, toluene disproportionation, transalkylation, hydrogenation and alkane oligomerization and aromatization. Some zeolite catalysts, especially those containing a Group VIII deposited metal, can be susceptible to sulfur poisoning.

Examples of the zeolite structure are MTW, FER, MEL, TON, MRE, MWW, MFI, BEA, MOR, LTL, or MTT. The term "ZSM-5" is used in this specification to mean a zeolite having an MFI structure. The zeolite can comprise ZSM-5, ZSM-11, ZSM-23, ferrierite, mordenite, or a combination comprising one or more of the foregoing. The zeolite can be from a family of pentasil zeolites that contain five membered ring units or pentasil units in the framework structure. Such zeolites include ZSM-5, ZSM-11, ZSM-23, and so on. The zeolite can be ZSM-5 or MFI (International Zeolite Association nomenclature of ZSM-5). The ZSM-5 zeolite has a two-dimensional pore structure with straight channels (5.4 Angstroms (Å)×5.6 Å) which are intersected by sinusoidal channels (5.1 Å×5.7 Å) with a maximum diameter of 9 Å at the intersection. The ZSM-5 zeolite catalysts and their preparation are described, for example, in U.S. Pat. No. 3,702,886. Such ZSM-5 zeolites are aluminosilicates that contain both silicon and aluminum in the crystalline structure. ZSM-11 is another pentasil aluminosilicate zeolite that is similar to ZSM-5.

The zeolite can contain elements other than aluminum and silicon in the crystalline framework, where at least some of the aluminum can be replaced by other trivalent elements and/or at least some of the silicon can be replaced by other tetravalent elements. Generally, zeolites are structures of $TO_4$ tetrahedra, which form a three dimensional network by sharing oxygen atoms where T represents tetravalent elements, such as silicon, and trivalent elements, such as aluminum. Tetravalent elements, such as germanium, tin, lead, zirconium, titanium, vanadium, or chromium, can be substituted for the silicon. Trivalent elements such as gallium, boron, indium, thallium, or iron, can be substituted for the aluminum. These tetravalent and trivalent elements would be in the framework of the zeolite crystal, also referred to as framework elements. Other elements which can be in the framework of the zeolite crystal are zinc and/or phosphorus.

A germanium zeolite includes silicon, germanium, and optionally aluminum in the crystalline framework of the zeolite structure, for example, a germanium zeolite can be an aluminosilicate zeolite having germanium in the framework and can preferably be a germanium ZSM-5 (Ge-ZSM-5) zeolite. A germanium zeolite can comprise a medium pore zeolite having an average pore size of 5 to 8 Å, a silica to alumina mole ratio ("SAR"; also referred to as $Si:Al_2$ mole ratio) of 125 to 200, and a germanium content of 0.1 to 3 wt %, preferably, 0.3 to 3 wt % based on the total weight of the final catalyst (excluding binder and extrusion aide). A germanium zeolite can comprise a zeolite having a structure such as MTW, FER, MEL, TON, MRE, MWW, MFI, BEA, MOR, LTL, or MTT.

The zeolite can be formed by preparing a mixture, allowing the mixture to form a gel, and crystallizing the zeolite therefrom. The mixture can comprise an aqueous solution of a germanium source (such as germanium dioxide), a sodium source (e.g., NaOH and/or NaCl), and an aluminum source (such as sodium aluminate, e.g., a sodium aluminate solution comprising alumina and sodium oxide), e.g., as a single aqueous solution or multiple solutions that are combined. For example, the zeolite can be formed by preparing two aqueous solutions, the first solution comprising a germanium source and a sodium source, and the second solution comprising an aluminum source, and combining said solutions. The mixture can comprise a silica source such as an ammonium or sodium ion stabilized colloidal silica, e.g. Ludox™ AS-30, Ludox™ AS-40, Ludox™ SM-30, or Ludox™ HS-30, commercially available from Sigma-Aldrich; or Nalco™ 1034A, Nalco™ 2326, Nalco™ 2327, Nalco™ 2329, or Nalco™ DVSZN002, commercially available from Nalco, wherein the colloidal silica can, for example, comprise 15 to 40 wt % silica, based upon a total weight of colloidal material.

The mixture can comprise an organic structure directing agent, which is incorporated in the microporous space of the crystalline network during crystallization, thus controlling the construction of the network and assisting to stabilize the structure through the interactions with, for example, the silicon and aluminum. Examples of the structure directing agent are organic amine and quaternary ammonium compounds and salts and cations thereof. Specifically, the structure directing agent can comprise at least one of tetra n-propyl ammonium hydroxide, tetra n-propyl ammonium bromide, tetra n-propyl ammonium chloride, tetraethyl ammonium hydroxide, tetraethylammonium bromide, tetramethylammonium chloride, hexamethyleneimine, 1,4-di(1'4'-diazabicyclo[2.2.2]octane)butane hydroxide, morpholine, cyclohexylamine, diethylethanolamine, N,N'-diisopropyl imidazolium cation, tetrabutylammonium compounds, di-n-propylamine (DPA), tripropylamine, triethylamine (TEA), triethanolamine, piperidine, 2-methylpyridine, N,N-dimethylbenzylamine, N,N-diethylethanolamine, dicyclohexylamine, N,N-dimethylethanolamine, choline cation, N,N'-dimethylpiperazine, 1,4-diazabicyclo(2,2,2)octane, 1,6-hexanediamine, N',N',N,N-tetramethyl-(1,6)hexanediamine, N-methyldiethanolamine, N-methylethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, 2-imidazolidone, a N-benzyl-1,4-diazabicyclo[2.2.2]octane cation, a 1-[1-(4-chlorophenyl)-cyclopropylmethyl]-1-ethyl-pyrrolidinium cation, a 1-ethyl-1-(1-phenyl-cyclopropylmethyl)-pyrrolidium cation, or 1,8-diaminooctane. The mixture can comprise a combination comprising one or more of the foregoing structure directing agents. The structure directing agent can comprise tetra-n-propyl ammonium hydroxide (TPAOH)). The mixture can have a structure directing agent to silica mole ratio of 0.01 to 1, preferably, 0.05 to 0.5.

The $Si:Al_2$ mole ratio of the mixture can be 175 to 290, preferably, 200 to 275, more preferably, 220 to 275. The Si:Ge mole ratio in the mixture can be 5 to 100, preferably, 15 to 50. The Na:Al mole ratio in the mixture can be 10 to 60, preferably, 12 to 40. The pH of the mixture can be adjusted to a value of greater than 9, preferably, greater than or equal to 10, more preferably, 10 to less than or equal to 13. For example, the pH of the mixture can be adjusted to a value of greater than or equal to 9.5, preferably, 9.5 to 12.5, more preferably, 10 to 12.5.

It is noted that although some zeolites are prepared with fluoride as a synthesis aid, this can be undesirable due to the potential high toxicity and corrosivity of fluoride, which can render it difficult and impractical to use in a commercial synthesis. Accordingly, the process disclosed herein can be fluoride free and hence, the final zeolite can be fluoride free (i.e., besides possible impurities, the zeolite has no fluoride). In other words, no fluoride is intentionally added during the process.

The mixture can then be crystallized, washed, and then calcined, to form the zeolite. The crystallization can occur at a temperature of 140 to 200° C., preferably, 160 to 180° C. The crystallization can occur for a time of up 6 days, preferably, 1 to 6 days, more preferably, 1.5 to 5 days. The crystallized zeolite can be washed with water and calcined. The zeolite can be calcined, e.g., to burn off one or more of the zeolite structure directing agents and any other decomposable materials that may be present. The zeolite can be calcined at a temperature of greater than or equal to 500° C., preferably, greater than or equal to 530° C., more preferably, greater than or equal to 550° C. The zeolite can be calcined at a temperature of 500 to 650° C. The zeolite can be calcined for greater than or equal to 0.5 hours (hr), preferably, greater than or equal to 1 hr, more preferably, greater than or equal to 2 hr. The zeolite can be calcined for 0.5 to 20 hr.

A noble metal can be deposited on the calcined zeolite, for example, by methods such as ion exchange, impregnation, and incipient wetness impregnation. The noble metal can be added to the calcined zeolite as a noble metal compound (e.g., a noble metal salt) that readily dissolves in water. For example, when the metal is platinum, the platinum source can be any applicable platinum source, such as chloroplatinic acid ($H_2PtCl_6 \cdot 6H_2O$), tetraamine platinum nitrate (($NH_2)_4Pt(NO_3)_2$), or a combination comprising at least one of the foregoing. The noble metal can be present in the final catalyst in a reduced amount of less than or equal to 3.0 wt % (as measured by x-ray fluorescence (XRF) technique), preferably, 0.05 to 3.0 wt %, more preferably, 0.25 to 3 wt %, more preferably, 0.2 to 2 wt %, even more preferably, 0.2 to 1.5 wt % based on the total weight of the catalyst (excluding binder and extrusion aide). The noble metal can comprise palladium, silver, platinum, gold, iridium, rhodium, ruthenium, or a combination comprising one or more of the foregoing, preferably, the noble metal can comprise platinum. The noble metal, such as platinum, can be deposited on the crystalline structure before or after the addition of the binder and shaping of the zeolite. After the noble metal has been added, the zeolite can be again heated, e.g., to about 300° C.

The method of making the present catalyst can be free of an ion-exchange step, for example, ion-exchange with an alkali metal, for example, cesium compound.

The zeolite can be heat treated after one or both of ion-exchanging with a base and after noble metal deposition to form the final catalyst. The catalyst can be heated at an elevated temperature of greater than or equal to 200° C., preferably, 200 to 400° C. for a period of time sufficient to decompose the metal salt(s). The heating time can be 0.5 to 10 hr, preferably, 0.5 to 5 hr. The catalyst can be further calcined, e.g., at a temperature of 200 to 400° C., preferably, 250 to 330° C., for a period of 0.5 to 20 hr, preferably, 1 to 20 hr, more preferably, 5 to 8 hr. The heat treatment and/or calcination can be under air, $O_2$, $N_2$, $H_2$ or a combination comprising at least one of the foregoing.

The final catalyst can be non-acidic. The final catalyst can have an SAR of greater than or equal to 125, preferably, 125 to 200, more preferably, 140 to 190. The final catalyst can have an Si:Ge mole ratio of 40 to 400, preferably, 50 to 300, more preferably, 80 to 200. The final catalyst can have an Na:Al mole ratio of 0.9 to 2.5, preferably, 1.2 to 2.2. The final catalyst can have a germanium content of 0.3 to 3 wt %, preferably, 0.4 to 2.5 wt %, more preferably, 0.6 to 1.5 wt %, even more preferably, 0.5 to 1.5 wt %, based upon a total weight of the final catalyst (excluding binder). The final catalyst can comprise one or more of 0.5 to 2 wt %, preferably, 1 to 2 wt % Na; less than or equal to 0.75 wt %, preferably, less than or equal to 0.7 wt %, more preferably, 0.4 to 0.7 wt % Al; less than 3 wt %, preferably, less than or equal to 2.5 wt %, more preferably, 0.4 to 1.5 wt % Ge; 0.05 to 3 wt %, preferably, 0.2 to 2 wt %, more preferably, 0.2 to 1.5 wt % Pt; or a combination comprising one or more of the foregoing; based upon a total weight of the final catalyst (excluding binder). The final catalyst can be free of cesium, for example, can comprise less than or equal to 0.1 wt %, for example, 0 wt % of cesium based on the total weight of the catalyst (excluding binder).

The chemical formula of the final catalyst can be represented by the formula I:

$$Pt_z[(0.9\text{-}2.5)M^+_y(SiO_2)(GeO_2)_x(AlO_2)_y]  \qquad (I)$$

wherein z is 0.00015 to 0.01; $M^+$ is an alkali metal, such as sodium, y is 0 to 0.02, preferably, 0.01 to 0.017; and x is 0.0025 to 0.025, preferably, 0.003 to 0.0125.

An additive can be added to the catalyst, which can comprise a binder and/or an extrusion aid to form a forming mixture. The binder can comprise inorganic oxide materials. The binder can comprise an aluminum- or silicon-containing material such as silica, alumina, clay, aluminum phosphate, silica-alumina, or a combination comprising at least one of the foregoing. The binder can comprise oxides of magnesium, titanium, zirconium, thorium, silicon, boron, and mixtures thereof; a clay, e.g., kaolin or montmorillonite; carbon, e.g., carbon black, graphite, activated carbon, polymers or charcoal; a metal carbide or nitride, e.g., molybdenum carbide, silicon carbide or tungsten nitride; a metal oxide hydroxide, e.g., boehmite; or a combination comprising one or more of the foregoing. The binder can comprise 0.5 to 30 wt %, preferably, 1 to less than 10 wt %, more preferably, 1 to 4.5 wt % non-silica oxides, based upon the total weight of the forming mixture.

The binder can comprise a colloidal silica binder, where the colloidal silica binders are acid, $NH_4^+$, or $Na^+$ stabilized colloidal silicas. The binder can comprise a solid silica that can comprise a crystalline silica, an amorphous silica, or a combination thereof. The binder can comprise at least one colloidal silica binder and at least one solid silica ($SiO_2$) binder. Some examples of solid silica binders include attapulgite, e.g. Min-U-Gel™ commercially available from Active Minerals International, Ultrasil™ commercially available from Sigma-Aldrich, those available from Degussa Corporation, and Davisil™-643 commercially available from Sigma-Aldrich.

The binder can have an average particle size of 10 to 25 nanometer (nm) based on a major axis. The binder can comprise a mixture of one or more binders and can comprise at least one solid binder and a mixture of colloidal binders, the mixtures of colloidal binders including at least 10 wt % of a colloidal binder having an average particle size of 10 to 30 nm based on a major axis, while the remaining colloidal binders can have an average particle size of 1 to 30 nm based on a major axis. The binder can comprise a mixture of at least 20 wt % of a colloidal binder having an average particle size of 10 to 30 nm based on a major axis, while the remaining binders can have an average particle size of 5 to 10 nm based on a major axis. The binder can have a surface area less than or equal to 250 meter square per gram ($m^2/g$), preferably, 250 to 100 $m^2/g$.

The binder can be present in the catalyst in an amount of up to 99 wt %, e.g., 1 to 99 wt %, preferably, 10 to 60 wt % based on the total weight of the forming mixture. The catalyst can comprise 15 to 50 wt %, preferably, 20 to 40 wt % of silica-containing binder material, more preferably, 20 to 30 wt %, based upon a total weight of the forming mixture.

The extrusion aid can comprise polyvinyl alcohol and/or polyacrylamide. For example, the extrusion aid can comprise a partially hydrolyzed poly(vinyl alcohol), e.g., produced commercially by hydrolysis of poly(vinyl acetate). When poly(vinyl acetate) is hydrolyzed the acetate groups ($COCH_3$) are substituted by hydrogen to form alcohol (—OH) groups along the polymer chain. Hereinafter, the term 'partially hydrolyzed' refers to a poly(vinyl acetate) that has been hydrolyzed by less than or equal to 90%. In the partially hydrolyzed poly(vinyl alcohol), acetate and alcohol groups are randomly distributed in the polymer chain. The partially hydrolyzed poly(vinyl alcohol) can have a weight average molecular weight (Mw) (for example, based on polycarbonate standards) of 500 to 500,000 g/mol, preferably, 10,000 to 200,000 g/mol. The partially hydrolyzed poly(vinyl alcohol) can be used in an amount of 0.1 to 5 wt %, preferably, 0.5 to 3 wt %, more preferably, 1 to 2 wt %, based on the total weight of the forming mixture.

The extrusion aid can comprise polyacrylamide. The polyacrylamide can have a weight average molecular weight (Mw) of 2 to 10 million g/mol, preferably, 2 to 7 million g/mol as determined by gel permeation chromatography based on polycarbonate standard. The polyacrylamide can be used in an amount of 0.1 to 5 wt %, preferably, 0.5 to 3 wt %, more preferably, 1 to 2 wt %, based on the total weight of the forming mixture. An example of a commercially available source of polyacrylamide is sold as under the trademark CYFLOC™ N-300 LMW Flocculant available from Cytec, West Peterson, N.J., which is a polyacrylamide having a Mw of 2 to 5 million g/mol as determined by gel permeation chromatography based on polycarbonate standard.

The forming mixture can be shaped (also referred to as formed) to result in a formed catalyst. The formed catalyst can be shaped by various forming processes such as pelletizing, tableting, extruding, and any other technique of forming a catalyst into a shape, as well as a combination comprising at least one of the foregoing processes. The resulting formed catalyst can be, for example, pellets or tablets. The formed catalyst can have cross-sections that are, for example, circular, oval, oblong, square, rectangular, diamond, polygonal, or a combination comprising one or more of the foregoing. Specific examples are 1/16 inch (1.6 millimeter (mm)) to 1/8 inch (3.2 mm) cylindrically shaped extrudates.

The catalyst can concurrently function as one or more of, a dehydrogenation, a dehydrocyclization, and an aromatization catalyst. Preferably, the catalyst can be used in a process of aromatization of alkanes, such as alkanes having six to twelve carbon atoms ($C_{6-12}$) per molecule, to produce aromatics, such as benzene, ethyl benzene, toluene, and xylenes. The contact between the alkane and the catalyst can be at a liquid hourly space velocity of 0.1 to 100 $hr^{-1}$, at a temperature of 200 to 950° C., preferably, 425 to 650° C., more preferably, 450 to 600° C., even more preferably, 475 to 550° C., at a pressure of 5 to 315 pounds per square inch absolute (psia). The present catalyst can work with a broad range of feeds, including paraffinic and olefinic compounds and/or naphthenes. For example, the feedstream to the reactor comprising the catalyst may comprise greater than or equal to 30 volume percent (vol %) paraffins (e.g., greater than or equal to 50 vol % paraffins), and optionally low, (i.e. less than or equal to 20 vol %, or even less than or equal to 10 vol %) naphthenes. The feedstream can comprise $C_{6-8}$ alkanes, either alone or as components in a mixture, i.e., in an amount of 0 to 100 vol % (e.g., greater than 0 up to 100 vol %, or greater than or equal to 10 vol %, preferably, greater than or equal to 20 vol %) for each of $C_6$, $C_7$, and $C_8$ alkane.

The feedstream can be a naphtha feed. The naphtha feed can be a refinery product comprising greater than or equal to 25 wt %, preferably, greater than or equal to 35 wt %, more preferably, greater than or equal to 50 wt % of $C_{5-9}$ aliphatic and cycloaliphatic hydrocarbons such as olefins and paraffins, and zero to 40 wt % $C_{6-13}$ aromatics (e.g., greater than zero to 40 wt % $C_{6-13}$ aromatics). The naphtha feed can comprise up to 1,000 parts per million by weight (ppm) sulfur, preferably, 1 to 500 ppm sulfur, more preferably, 1 to 200 ppm sulfur, even more preferably, 1 to 50 ppm sulfur, where the term sulfur refers to elemental sulfur as well as sulfur compounds (such as organosulfides and heterocyclic benzothiophenes). The naphtha feed can comprise up to 100 parts per million by weight (ppm) of nitrogen compounds.

The following examples are provided to illustrate the improved catalyst. The examples are merely illustrative and are not intended to limit devices made in accordance with the disclosure to the materials, conditions, or process parameters set forth therein.

EXAMPLES

The materials used in the following examples are described in Table 1. Unless specifically stated otherwise, the materials are used in the form as set forth in Table 1 and the quantities identified in the examples are based upon that form.

TABLE 1

| Component | Source |
|---|---|
| Sodium hydroxide (NaOH) 50 wt % aqueous solution | Sigma-Aldrich |
| Germanium dioxide | Umicore |
| Sodium aluminate solution | Southern Ionics |
| Tetra-n-amine platinum nitrate (($NH_3)_4Pt(NO_3)_2$, 49.9 wt % Pt) | Sigma-Aldrich |
| Tetra-n-propyl aluminum hydroxide (TPAOH); | SACHEM |
| Nalco 2326 (15 wt % silica in a colloidal state) | Nalco Company |
| Glacial acetic acid | Sigma-Aldrich |
| Cesium nitrate ($CsNO_3$) | Cabot Specialty Fluids |

Example 1: Catalyst Preparation

The following procedure was used to synthesize the catalysts used in Examples 1-21, where the amounts were varied according to the specific example and where the amounts in the final catalysts are shown in the corresponding tables; the specific numbers shown in the procedure are for Example 1. Solution 1 was made by diluting a 50 wt % NaOH solution with deionized water and subsequently dissolving in germanium dioxide. Solution 2 was made by diluting a sodium aluminate solution (23.6 wt % alumina and 19.4 wt % sodium oxide) with deionized water. The two solutions were combined and mixed. TPAOH was added and stirred for about 10 minutes (min). Ludox AS-40 was added all at once and the gel was stirred for 2.5 hr to make it homogeneous. Glacial acetic acid was added as needed to adjust the pH of the mixture.

The gel was loaded into a 1 liter (L) stainless steel autoclave and heated at 160° C. for 3 days with stirring. The solids were then filtered from the mother liquor and washed with deionized water. The solid was calcined at 550° C. for 10 hr in an oven with air flow to result in a Ge-ZSM-5 zeolite. The MFI structure of the solid was confirmed by measuring the powder X-ray diffraction pattern.

Where the final catalyst comprises platinum, incipient wetness impregnation was carried out by adding, dropwise, a solution of tetraammineplatinum nitrate dissolved in deionized water to the Ge-ZSM-5 zeolite. The material was dried for 1 hr at 110° C. in an oven and then calcined at 280° C. for 3 hr. Elemental analysis for each catalyst is shown in the corresponding tables.

The catalyst powder was pressed and sized to 20-40 mesh. 0.25 cubic centimeters ($cm^3$) (0.131 grams (g)) of the sized catalyst was mixed with 1.75 $cm^3$ of inert silicon carbide chips and was heated at 460° C. for 1 hr in flowing $H_2$. The temperature was then raised to 515° C. and catalytic testing, where performed, was started. A gas mixture was formed by vaporizing n-hexane into a stream of flowing hydrogen at a temperature of approximately 150° C. This gas mixture was passed through the reactor, which was maintained at 515° C. by an external heating jacket. The reaction products were analyzed by gas chromatography. Products ranging in size from methane to dimethylnaphthalene were observed. For the purposes of calculating conversion and selectivity, $C_6$ isomerization and dehydrogenation products were considered to be unreacted. The selectivities, $S_{50}$ (i.e., catalyst selectivity after 50 hours on stream) reported were calculated as the sum of benzene, toluene, and xylenes (BTX) produced divided by the sum of benzene and all $C_{1-5}$ and $C_{7+}$ materials recovered. These selectivities are presented on a molar $C_6$ basis. The conversions, $X_{50}$ (i.e., catalyst activity after 50 hours on stream), reported were calculated as the fraction of n-hexane feed converted to benzene, toluene, xylenes, and all $C_{1-5}$ and $C_{7+}$ materials recovered.

Table 2 summarizes the synthesis data for Example 1 and shows that this material has excellent catalytic performance, with a conversion of 31% and an aromatics selectivity of 96% at the conditions described above. The weight percent values of the respective components are based on the total weight of the final catalyst.

TABLE 2

| Example | 1 |
|---|---|
| Mixture composition | |
| $SiO_2$:$Al_2O_3$ (mole ratio) | 225 |
| Na:Al (mole ratio) | 11.23 |
| $Na_2O$:$SiO_2$ (mole ratio) | 0.05 |
| TPAOH:$SiO_2$ (mole ratio) | 0.10 |
| $H_2O$:$SiO_2$ (mole ratio) | 23 |
| $SiO_2$:Ge (mole ratio) | 30 |
| $OH^-$:$SiO_2$ (mole ratio) | 0.20 |
| pH | 12.0 |

TABLE 2-continued

| Example | 1 |
|---|---|
| Final catalyst composition | |
| $SiO_2$:$Al_2O_3$ (molar ratio) | 195 |
| Na (wt %) | 0.74 |
| Si (wt %) | 43.94 |
| Al (wt %) | 0.45 |
| Ge (wt %) | 1.11 |
| Cs (wt %) | 0 |
| Pt (wt %) | 1.03 |
| Catalytic performance | |
| $X_{50}$ | 31 |
| $S_{50}$ | 96 |

Examples 2-7: Varying the Si:$Al_2$ Mole Ratio

Six catalysts as shown in Examples 2-7 were made and tested for conversion and selectivity, where the Si:$Al_2$ mole ratio in the mixture was varied. Specifically, the process was the same as set forth for Example 1 except that the synthesis mixtures used in Examples 2-7 had Si:$Al_2$ mole ratios of 110, 170, 225, 250, 275, and 300, respectively. Correspondingly, the Si:$Al_2$ mole ratios in the final catalyst of Examples 2-7 were 60, 102, 151, 178, 189, and 206, respectively. The results are shown in Table 3.

Table 3 shows that improved conversion and selectivity are observed when the Si:$Al_2$ mole ratio in the final catalyst is 151 to 189, where Example 4, 5, and 6 resulted in conversions of 33%, 23%, and 31%, respectively, and selectivities of 94%, 96%, and 96%, respectively.

TABLE 3

| Example | 2 | 3 | 4 | 5 | 6 | 7 |
|---|---|---|---|---|---|---|
| Mixture composition | | | | | | |
| Si:$Al_2$ (mole ratio) | 110 | 170 | 225 | 250 | 275 | 300 |
| Na:Al (mole ratio) | 24.71 | 24.71 | 24.71 | 27.5 | 30.25 | 24.72 |
| Si:Ge (mole ratio) | 29.83 | 29.84 | 29.84 | 29.83 | 29.84 | 29.84 |
| TPAOH:$SiO_2$ (mole ratio) | 0.10 | 0.10 | 0.10 | 0.10 | 0.10 | 0.14 |
| $H_2O$:$SiO_2$ (mole ratio) | 23.85 | 23.85 | 23.85 | 23.85 | 23.85 | 24.50 |
| pH | 12.0 | 12.1 | 12.0 | 12.2 | 12.4 | 12.1 |
| Final catalyst composition | | | | | | |
| Si:$Al_2$ (mole ratio) | 60 | 102 | 151 | 178 | 189 | 206 |
| Na:Al (mole ratio) | 0.79 | 1.01 | 1.64 | 2.10 | 2.48 | 2.65 |
| Si:Ge (mole ratio) | 243 | 280 | 193 | 186 | 168 | 178 |
| Na (wt %) | 0.93 | 0.74 | 0.81 | 0.86 | 0.95 | 0.97 |
| Si (wt %) | 43.08 | 45.27 | 45.47 | 44.39 | 44.11 | 45.87 |
| Al (wt %) | 1.39 | 0.86 | 0.58 | 0.48 | 0.45 | 0.43 |
| Ge (wt %) | 0.46 | 0.42 | 0.61 | 0.62 | 0.68 | 0.67 |
| Catalytic performance | | | | | | |
| $X_{50}$ | 8 | 28 | 33 | 23 | 31 | 2 |
| $S_{50}$ | 70 | 84 | 94 | 96 | 96 | 73 |

TABLE 4

| Example | 8 | 9 | 10 | 11 |
|---|---|---|---|---|
| Mixture composition | | | | |
| Si:$Al_2$ (mole ratio) | 225 | 225 | 225 | 225 |
| Na:Al (mole ratio) | 24.69 | 24.69 | 24.71 | 24.71 |
| Si:Ge (mole ratio) | 15 | 22 | 29.8 | 50 |
| TPAOH:$SiO_2$ (mole ratio) | 0.10 | 0.10 | 0.10 | 0.10 |

TABLE 4-continued

| Example | 8 | 9 | 10 | 11 |
|---|---|---|---|---|
| $H_2O:SiO_2$ (mole ratio) | 23.85 | 23.85 | 23.85 | 23.88 |
| pH | 12.0 | 12.0 | 12.0 | 12.0 |
| Final catalyst composition | | | | |
| $Si:Al_2$ (mole ratio) | 168 | 159 | 151 | 139 |
| Na:Al (mole ratio) | 1.82 | 1.72 | 1.64 | 1.98 |
| Si:Ge (mole ratio) | 88 | 141 | 193 | 287 |
| Na (wt %) | 0.79 | 0.79 | 0.81 | 1.06 |
| Si (wt %) | 44.50 | 44.64 | 45.47 | 45.42 |
| Al (wt %) | 0.51 | 0.54 | 0.58 | 0.63 |
| Ge (wt %) | 1.31 | 0.82 | 0.61 | 0.41 |
| Catalytic performance | | | | |
| $X_{50}$ | 36 | 33 | 33 | 24 |
| $S_{50}$ | 94 | 94 | 94 | 95 |

Examples 8-11: Varying the Si:Ge Mole Ratio

Four catalysts as shown in Examples 8-11 were made and tested for conversion and selectivity, where the Si:Ge mole ratio in the mixture was varied. Specifically, the synthesis mixtures used in Examples 8-11 had Si:Ge mole ratios of 15, 22, 29.8, and 50, respectively. Correspondingly, the Si:Ge mole ratios in the final catalyst of Examples 8-11 were 88, 141, 193, and 287, respectively. The results are shown in Table 4.

Table 4 shows that over all the Si:Ge mole ratios tested, the catalysts of Examples 8-11 displayed high conversions of 24 to 36% and high selectivities of 94 to 95%.

Examples 12-16: Varying the pH of the Mixture

Five catalysts as shown in Examples 12-16 were made and tested for conversion and selectivity, where the pH of the mixture was varied. Specifically, the pH values of the mixtures of Examples 12-16 were 9.1, 10.0, 11.0, 12.0, and 13.0, respectively. The results are shown in Table 5.

TABLE 5

| Example | 12 | 13 | 14 | 15 | 16 |
|---|---|---|---|---|---|
| Mixture composition | | | | | |
| $Si:Al_2$ (mole ratio) | 225 | 225 | 225 | 225 | 225 |
| Na:Al (mole ratio) | 24.68 | 24.71 | 24.71 | 24.71 | 24.69 |
| Si:Ge (mole ratio) | 29.84 | 29.84 | 29.84 | 29.84 | 29.84 |
| $TPAOH:SiO_2$ (mole ratio) | 0.10 | 0.10 | 0.10 | 0.10 | 0.42 |
| $H_2O:SiO_2$ (mole ratio) | 23.85 | 23.85 | 23.85 | 23.85 | 28.55 |
| pH | 9.1 | 10.0 | 11.0 | 12.0 | 13.0 |
| Final catalyst composition | | | | | |
| $Si:Al_2$ (mole ratio) | 204 | 211 | 177 | 151 | 106 |
| Na:Al (mole ratio) | 0.28 | 1.69 | 1.92 | 1.64 | 0.79 |
| Si:Ge (mole ratio) | 42 | 49 | 92 | 193 | 466 |
| Na (wt %) | 0.10 | 0.59 | 0.80 | 0.81 | 0.55 |
| Si (wt %) | 44.36 | 44.90 | 44.90 | 45.47 | 44.89 |
| Al (wt %) | 0.42 | 0.41 | 0.49 | 0.58 | 0.82 |
| Ge (wt %) | 2.74 | 2.40 | 1.27 | 0.61 | 0.25 |
| Catalytic performance | | | | | |
| $X_{50}$ | 3 | 27 | 23 | 33 | 16 |
| $S_{50}$ | 53 | 92 | 94 | 94 | 77 |

Table 5 shows that improved conversion and selectivity are observed when the pH of the mixture is greater than 9.5, preferably, 10 to 12, where Examples 13-15 resulted in conversions of 27%, 23%, and 33%, respectively, and selectivities of 92%, 94%, and 94%, respectively.

TABLE 6

| Example | 17 | 18 | 19 | 20 | 21 |
|---|---|---|---|---|---|
| Mixture composition | | | | | |
| $Si:Al_2$ (mole ratio) | 225 | 225 | 225 | 225 | 225 |
| Na:Al (mole ratio) | 6.97 | 13.35 | 24.71 | 40.0 | 45.0 |
| Si:Ge (mole ratio) | 29.84 | 29.84 | 29.84 | 29.84 | 29.84 |
| $TPAOH:SiO_2$ (mole ratio) | 0.12 | 0.13 | 0.10 | 0.12 | 0.10 |
| $H_2O:SiO_2$ (mole ratio) | 23.73 | 24.11 | 23.85 | 24.09 | 23.85 |
| pH | 12.1 | 12.1 | 12.0 | 12.1 | 12.1 |
| Final catalyst composition | | | | | |
| $Si:Al_2$ (mole ratio) | 69 | 177 | 151 | 141 | 126 |
| Na:Al (mole ratio) | 0.32 | 2.10 | 1.64 | 1.73 | 1.62 |
| Si:Ge (mole ratio) | 106 | 139 | 193 | 141 | 288 |
| Na (wt %) | 0.34 | 0.86 | 0.81 | 0.90 | 0.94 |
| Si (wt %) | 44.94 | 43.93 | 45.47 | 44.55 | 44.48 |
| Al (wt %) | 1.26 | 0.48 | 0.58 | 0.61 | 0.68 |
| Ge (wt %) | 1.10 | 0.82 | 0.61 | 0.82 | 0.40 |
| Catalytic performance | | | | | |
| $X_{50}$ | 19 | 39 | 33 | 36 | 47 |
| $S_{50}$ | 7 | 93 | 94 | 95 | 91 |

Examples 17-21: Varying the Na:Al Mole Ratio

Five catalysts as shown in Examples 17-21 were made and tested for conversion and selectivity, where the Na:Al mole ratio in the mixture was varied. Specifically, Examples 17-21 had Na:Al mole ratios of 6.97, 13.35, 24.71, 40.0, and 45.0, respectively. Correspondingly, the Na:Al mole ratios in the final catalyst of Examples 17-21 were 0.32, 2.10, 1.64, 1.73, and 1.62, respectively. The results are shown in Table 6.

Table 6 shows that improved conversion and selectivity are observed when the Na:Al mole ratio in the final catalyst is greater than 0.9, where Examples 18, 19, 20, and 21 resulted in conversions of 39%, 33%, 36%, and 47%, respectively, and selectivities of 93%, 94%, 95%, and 91%, respectively.

Comparative Examples 22-23: Comparison to Known Catalysts

Comparative Example 22 was prepared according to the procedure in U.S. Pat. No. 7,902,413, as follows: Solution #1 was made by diluting 15.84 g of 50 wt % NaOH solution with 131.25 g of deionized (DI) water and subsequently dissolving 7.11 g of germanium dioxide. Solution #2 was made by diluting 3.84 g sodium aluminate solution (23.6 wt % alumina and 19.4 wt % sodium oxide) with 153.9 g DI water. Solution #1 was added to 150.0 g Ludox AS-40 (40 wt % silica in a colloidal state) and stirred for 7 minutes. Solution #2 was added, and the resulting mixture was stirred for 20 minutes. 105.42 g of tetra-n-propyl ammonium hydroxide (TPAOH) was added and the mixture was stirred for 60 minutes. Finally, 23.34 g of glacial acetic acid was added to the mixture to adjust the pH to 9.2. This mixture was loaded into a 1 L stainless steel autoclave and heated at 160° C. for 36 hours with stirring. Subsequently, the solids obtained were filtered from the mother liquor and washed with deionized water. The solid was calcined at 550° C. for 10 hours in an oven with air flow. The MFI structure of the solid was confirmed by measuring the powder X-ray diffraction pattern.

A portion of the resulting Ge-ZSM-5 zeolite was ion-exchanged with an aqueous solution of $CsNO_3$ (0.5 M) in 4 steps at room temperature and then filtered. The filtrate was then washed on filter with distilled water and calcined for 3 hours at 280° C. in air. Incipient wetness impregnation was carried out by dropwise addition of a solution of tetraammineplatinum nitrate dissolved in deionized water to the Ge-ZSM-5 zeolite. The material was dried at 90° C. in an oven and then calcined at 280° C. for 3 hr.

Comparative Example 23 was prepared by the same procedure, except that only half as much sodium aluminate (1.92 g) was used. For this sample, 23.0 g of acetic acid was required to adjust the pH to 9.2.

Comparative Examples 22 and 23 were tested according to the same procedures used for Examples 1-21. Results of elemental analysis and catalyst testing are shown in Table 7.

As can be seen in Table 7, Comparative Example 22, which was prepared at pH 9, contains a higher content of aluminum and germanium and has been base-exchanged with cesium, is less active and less selective than Examples 4-6, 8-11, 14, 15, 19, and 20; Examples 13 and 18 have similar selectivity to Comparative Example 22 but have higher conversion.

As can be seen in Table 7, Comparative Example 23, which is prepared at pH 9 and with Cs-base exchange but with less aluminum, has an unacceptably low conversion and selectivity for n-hexane conversion.

TABLE 7

| Example | 22 | 23 |
|---|---|---|
| Mixture composition | | |
| Si:Al$_2$ (mole ratio) | 112 | 225 |
| Na:Al (mole ratio) | 12.49 | 23.65 |
| Si:Ge (mole ratio) | 14.69 | 14.69 |
| TPAOH:SiO$_2$ (mole ratio) | 0.21 | 0.21 |
| H$_2$O:SiO$_2$ (mole ratio) | 24.95 | 24.89 |
| pH | 9.22 | 9.15 |
| Final catalyst composition | | |
| Si:Al$_2$ (mole ratio) | 103 | 195 |
| Cs:Al (mole ratio) | 1.17 | 1.76 |
| Si:Ge (mole ratio) | 25 | 18 |
| Cs (wt %) | 4.38 | 3.46 |
| Si (wt %) | 40.60 | 40.48 |
| Al (wt %) | 0.76 | 0.40 |
| Ge (wt %) | 4.19 | 5.69 |
| Catalytic performance | | |
| $X_{50}$ | 20 | 3 |
| $S_{50}$ | 93 | 38 |

Set forth below are some embodiments of the present catalyst and methods of making and using the same.

Embodiment 1: a method for making a catalyst, comprising: forming a mixture comprising a germanium source, an alkali metal source, an aluminum source, and a silica source, wherein the mixture has a pH; adjusting the pH of the mixture to a value of greater than or equal to 9.5, preferably, greater than 9.5; crystallizing and calcining the mixture to form a zeolite; depositing platinum on the zeolite; and calcining the zeolite to form the final catalyst. The final catalyst is non-acidic and has an aluminum content of less than or equal to 0.75 wt % based on the total weight of the final catalyst excluding any binder and extrusion aide and a final Si:Al$_2$ mole ratio of greater than or equal to 125.

Embodiment 2: the method of Embodiment 1, further comprising allowing the mixture to form a gel after adjusting the pH.

Embodiment 3: the method of any of Embodiments 1-2, wherein the forming of the mixture comprises: forming a first aqueous solution, wherein the first solution comprises the germanium source and the alkali metal source; forming a second aqueous solution, wherein the second solution comprises the aluminum source; combining the first and second aqueous solutions to form a combined solution; and adding the silica source to the combined solution to form the mixture.

Embodiment 4: the method of any of Embodiments 1-3, wherein the mixture has a mixture Si:Al$_2$ mole ratio of 175 to 290.

Embodiment 5: the method of any of Embodiments 1-4, wherein the mixture has a mixture Si:Ge mole ratio of 5 to 100.

Embodiment 6: the method of any of Embodiments 1-5, wherein the mixture has a Na:Al mole ratio of 10 to 60.

Embodiment 7: the method of any of Embodiments 1-6, wherein the mixture has a mixture Si:Al$_2$ mole ratio of 175 to 290, a mixture Si:Ge mole ratio of 5 to 100, and a mixture Na:Al mole ratio of 10 to 60.

Embodiment 8: the method of any of Embodiments 1-7, wherein the mixture has a mixture Si:Al$_2$ mole ratio of 200 to 275.

Embodiment 9: the method of Embodiment 8, wherein the mixture Si:Al$_2$ mole ratio is 220 to 275.

Embodiment 10: the method of any of Embodiments 1-9, wherein the mixture has a mixture Si:Ge mole ratio of 15 to 50.

Embodiment 11: the method of any of Embodiments 1-10, wherein the mixture has a mixture Na:Al mole ratio of 12 to 40.

Embodiment 12: the method of any of Embodiments 1-11, wherein the zeolite is a ZSM-5 zeolite.

Embodiment 13: the method of any of Embodiments 1-12, wherein the final Si:Al$_2$ mole ratio is 125 to 200, preferably, 140 to 190, more preferably, 151 to 189.

Embodiment 14: the method of any of Embodiments 1-13, wherein the final catalyst has one or both of a final Si:Ge mole ratio of 40 to 400 and a final Na:Al mole ratio of 0.9 to 2.5.

Embodiment 15: the method of Embodiment 14, wherein the final Si:Ge mole ratio is 50 to 300.

Embodiment 16: the method of any of Embodiments 14-15, wherein the Si:Ge mole ratio is 80 to 200.

Embodiment 17: the method of any of Embodiments 14-16, wherein the Na:Al mole ratio is 1.2 to 2.2.

Embodiment 18: the method of any of Embodiments 1-17, wherein the final catalyst comprises a germanium content of less than or equal to 3.0 wt %.

Embodiment 19: the method of any of Embodiments 1-18, wherein the final catalyst comprises one or more of a Ge content of 0.1 to 3 wt %, an Na content of 0.5 to 2 wt %, and a Pt content of 0.05 to 3 wt %, wherein the wt % values are based on the total weight of the final catalyst excluding any binder and extrusion aide.

Embodiment 20: the method of Embodiment 19, wherein the Ge content is 0.3 to 3, preferably, 0.4 to 2.5, more preferably, 0.6 to 1.5, even more preferably, 0.5 to 1.5 wt %.

Embodiment 21: the method of any of Embodiments 19-20, wherein the sodium content is 1 to 2 wt %.

Embodiment 22: the method of any of Embodiments 19-21, wherein the platinum content is 0.2 to 2, preferably, 0.2 to 1.5 wt %.

Embodiment 23: the method of any of Embodiments 1-22, wherein the method does not include an ion-exchange step with an alkali metal and/or an alkali earth metal.

Embodiment 24: the method of any of Embodiments 1-23, wherein the final catalyst is free of cesium.

Embodiment 25: the method of any of Embodiments 1-24, wherein the alkali metal source comprises at least one of a sodium source and a potassium source.

Embodiment 26: the method of any of Embodiments 1-25, wherein the alkali metal source comprises at least one of NaOH and NaCl.

Embodiment 27: the method of any of Embodiments 1-26, wherein the pH is 9.5 to 12.5.

Embodiment 28: the method of any of Embodiments 1-27, wherein the pH is 10 to 12.5.

Embodiment 29: the method of any of Embodiments 1-28, wherein the mixture further comprises a structure directing agent.

Embodiment 30: the method of Embodiment 29, wherein the mixture has a structure directing agent to silica mole ratio of 0.01 to 1.

Embodiment 31: the method of Embodiment 30, wherein the structure directing agent to silica mole ratio is 0.05 to 0.5.

Embodiment 32: the method of any of Embodiments 29-31, wherein the structure directing agent comprises TPAOH.

Embodiment 33: a catalyst prepared by any of the Embodiments 1-32.

Embodiment 34: a method of for the aromatization of hydrocarbons comprising: contacting an alkane containing 6 to 12 carbon atoms per molecule with the catalyst of Embodiment 33 or 35 or 36.

Embodiment 35: a catalyst comprising: a zeolite comprising Si, Al, and Ge in the framework with Pt deposited thereon; wherein the catalyst has an Si:Al$_2$ mole ratio of greater than or equal to 125, an Si:Ge mole ratio of 40 to 400, and an Na:Al mole ratio of 0.9 to 2.5, wherein the catalyst has an aluminum content of less than or equal to 0.75 wt %, wherein the catalyst is non-acidic.

Embodiment 36: the catalyst of Embodiment 35, wherein the Ge is present in an amount of 0.3 to 3 wt %, and/or the Na is present in an amount of 0.5 to 2 wt % and/or the Pt is present in an amount of 0.05 to 3 wt %, wherein the wt % values are based on the total weight of the final catalyst excluding any binder and extrusion aide.

Embodiment 37: a method for the aromatization of hydrocarbons comprising: contacting an alkane containing 6 to 12 carbon atoms per molecule with the catalyst of any of Embodiments 33, 35, or 36.

Embodiment 38: a method for the aromatization of hydrocarbons comprising: contacting an alkane containing 6 to 12 carbon atoms per molecule with a catalyst comprising: a zeolite comprising Si, Al, and Ge in the framework with Pt deposited thereon; wherein the catalyst has an Si:Al$_2$ mole ratio of greater than or equal to 125, an Si:Ge mole ratio of 40 to 400, and an Na:Al mole ratio of 0.9 to 2.5, wherein the catalyst has an aluminum content of less than or equal to 0.75 wt % excluding any binder and extrusion aide.

Embodiment 39: the method of Embodiment 39, wherein the Ge is present in an amount of 0.3 to 3 wt %, and/or the Na is present in an amount of 0.5 to 2 wt % and/or the Pt is present in an amount of 0.05 to 3 wt %, wherein the wt % values are based on the total weight of the final catalyst excluding any binder and extrusion aide.

In general, the invention can alternately comprise, consist of, or consist essentially of, any appropriate components herein disclosed. The invention can additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, more preferably, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The term "or" means "and/or" unless clearly indicated otherwise by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

Disclosure of a narrower range in addition to a broader range is not a disclaimer of the broader range.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. In addition, it is to be understood that the described elements may be combined in any suitable manner in the various embodiments.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The invention claimed is:

1. A method for the aromatization of hydrocarbons comprising:
    contacting a hydrocarbon feedstream with a catalyst;
    wherein the catalyst comprises a zeolite comprising Si, Al, and Ge in the framework with Pt deposited thereon; wherein the zeolite has an average pore size of 5 to 8 Å; and wherein the zeolite further comprises Na; and wherein the catalyst has an Si:Al$_2$ mole ratio of greater than or equal to 125, an Si:Ge mole ratio of 40 to 400, and an Na:Al mole ratio of 0.9 to 2.5, wherein the catalyst has an aluminum content of less than or equal to 0.75 wt % excluding any binder and extrusion aide.

2. The method of claim 1, wherein the hydrocarbon feedstream comprises an olefinic compound.

3. The method of claim 1, wherein the hydrocarbon feedstream comprises an alkane compound.

4. The method of claim 3, wherein the alkane compound comprises a $C_{6-12}$ alkane.

5. The method of claim 3, wherein the alkane compound comprises a $C_{6-8}$ alkane.

6. The method of claim 5, wherein the feed stream comprises 20 to 100 vol % of at least one of the $C_6$, $C_7$, or $C_8$ alkane.

7. The method of claim 1, wherein the hydrocarbon feedstream comprises naphthene.

8. The method of claim 1, wherein the hydrocarbon feedstream comprises a naphtha feed.

9. The method of claim 8, wherein the naphtha feed comprises up to 1,000 parts per million by weight sulfur and/or up to 100 parts per million by weight of nitrogen compounds.

10. The method of claim 1, wherein the Ge is present in an amount of 0.3 to 3 wt %, and/or the Na is present in an amount of 0.5 to 2 wt % and/or the Pt is present in an amount of 0.05 to 3 wt %, wherein the wt % values are based on the total weight of the catalyst excluding any binder and extrusion aide.

11. The method of claim 1, wherein the catalyst has a Ge content of 0.1 to 3 wt % based on the total weight of the final catalyst excluding any binder and extrusion aide.

12. The method of claim 1, wherein the catalyst comprises Al in an amount of 0.45 to 0.7 wt % based on the total weight of the catalyst excluding any binder and extrusion aide.

13. The method of claim 1, wherein the Na:Al mole ratio is 1.2 to 2.2.

14. The method of claim 1, wherein the $Si:Al_2$ mole ratio is 125 to 211.

15. The method of claim 1, wherein the Si:Ge mole ratio is 50 to 300.

16. The method of claim 1, wherein the zeolite is a ZSM-5 zeolite.

17. The method of claim 1, wherein the contacting occurs at a liquid hourly space velocity of 0.1 to 100 $hr^{-1}$, a temperature of 200 to 950° C., and a pressure of 5 to 315 pounds per square inch absolute.

18. A method for the aromatization of hydrocarbons comprising:
   contacting an olefinic feedstream with a catalyst;
   wherein the catalyst comprises a zeolite comprising Si, Al, and Ge in the framework with Pt deposited thereon; wherein the zeolite further comprises Na; wherein the zeolite has an average pore size of 5 to 8 Å; and
   wherein the catalyst has an $Si:Al_2$ mole ratio of greater than or equal to 125, an Si:Ge mole ratio of 40 to 400, and an Na:Al mole ratio of 0.9 to 2.5, wherein the catalyst has an aluminum content of less than or equal to 0.75 wt % excluding any binder and extrusion aide.

* * * * *